US010985464B2

United States Patent
Jain et al.

(10) Patent No.: US 10,985,464 B2
(45) Date of Patent: Apr. 20, 2021

(54) MINIATURIZED INDUCTIVE LOOP ANTENNA WITH DISTRIBUTED REACTIVE LOADS

(71) Applicant: Verily Life Sciences LLC, South San Francisco, CA (US)

(72) Inventors: Sidharath Jain, Burlingame, CA (US); Stephen O'Driscoll, San Francisco, CA (US); Christian Gutierrez, Pacifica, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

(21) Appl. No.: 16/528,290

(22) Filed: Jul. 31, 2019

(65) Prior Publication Data

US 2021/0036425 A1    Feb. 4, 2021

(51) Int. Cl.
*H01Q 7/00*    (2006.01)
*H01Q 1/27*    (2006.01)
(Continued)

(52) U.S. Cl.
CPC ............... *H01Q 7/005* (2013.01); *A61F 2/16* (2013.01); *G02C 7/04* (2013.01); *G02C 11/10* (2013.01);
(Continued)

(58) Field of Classification Search
CPC ........ H01Q 7/005; H01Q 1/273; G02C 11/10; G02C 7/04; A61F 2/16; A61F 2250/0096; A61F 2250/0001
See application file for complete search history.

(56) References Cited

U.S. PATENT DOCUMENTS 8,857,983 B2   10/2014   Pugh et al.
9,442,310 B2   9/2016   Biederman et al.
(Continued)

FOREIGN PATENT DOCUMENTS

EP    2979622 A1    2/2016
WO   2011100618 A1   8/2011

OTHER PUBLICATIONS

International Search Report and Written Opinion dated Sep. 18, 2020 in International Patent Application No. PCT/US2020/40703, 12 pages.

*Primary Examiner* — Seokjin Kim
(74) *Attorney, Agent, or Firm* — Christensen O'Connor Johnson Kindness PLLC (57) ABSTRACT

A device for implanting into, or mounting onto, a body includes an enclosure, an inductive loop antenna disposed on a surface within the enclosure, and an integrated circuit (IC) disposed within the enclosure and coupled to the inductive loop antenna. The inductive loop antenna includes one or more distributed reactive loads disposed along the inductive loop antenna that adjust a reactance of the inductive loop antenna. The one or more distributed reactive loads include signal trace sections that run along, or adjacent to, the surface upon which the inductive loop antenna is disposed. The IC includes communication circuitry coupled to the inductive loop antenna to wirelessly communicate over the inductive loop antenna. The one or more distributed reactive loads adjust the reactance of the inductive loop antenna to improve conjugate reactance matching of the inductive loop antenna to the IC.

21 Claims, 7 Drawing Sheets

(51) Int. Cl.
*G02C 7/04* (2006.01)
*A61F 2/16* (2006.01)
*G02C 11/00* (2006.01)

(52) U.S. Cl.
CPC ...... *H01Q 1/273* (2013.01); *A61F 2250/0001* (2013.01); *A61F 2250/0096* (2013.01)

(56) References Cited

U.S. PATENT DOCUMENTS

| | | | |
|---|---|---|---|
| 9,825,364 B2 | 11/2017 | O'Driscoll | |
| 2013/0194540 A1* | 8/2013 | Pugh | G02C 7/049 351/159.03 |
| 2013/0257666 A1* | 10/2013 | Desclos | H01Q 9/16 343/747 |
| 2013/0293354 A1* | 11/2013 | Vemagiri | G06K 19/0723 340/10.1 |
| 2016/0104935 A1 | 4/2016 | Hung | |
| 2017/0227792 A1* | 8/2017 | Starner | A61B 5/1103 |
| 2017/0245444 A1 | 8/2017 | Savuoja et al. | |
| 2018/0031867 A1 | 2/2018 | Lee et al. | |
| 2018/0076524 A1 | 3/2018 | O'Driscoll | |
| 2019/0094570 A1 | 3/2019 | Jow et al. | |

* cited by examiner

DISTRIBUTED SERIES CAPACITANCE ($C_{DS}$)

DISTRIBUTED SHUNT (PARALLEL) CAPACITANCE ($C_{DP}$)

DISTRIBUTED SERIES INDUCTANCE ($L_D$)

MINIATURIZED INDUCTIVE LOOP ANTENNA WITH DISTRIBUTED REACTIVE LOADS

TECHNICAL FIELD

This disclosure relates generally to antenna design, and in particular but not exclusively, relates to antenna design for small antennas.

BACKGROUND INFORMATION

For devices that employ near field wireless powering and/or wireless communication links, such as UHF or higher frequencies, tuning or impedance matching networks are often required to deliver good power transfer and impedance matching for strong signal delivery. These tuning or impedance matching networks are often implemented with discrete, lump capacitors or inductors (e.g., surface mount components) that couple directly to the antenna. In very small form factor systems, such as eye worn devices or body implantable devices, adding a discrete, lump capacitor or inductor component may not be possible due to height, weight, fit, and/or comfort restrictions.

Conventionally, to avoid the use of discrete, lump components for impedance matching, one may employ a tunable or fixed capacitance circuit that is internally integrated into an integrated circuit, and which tunes the antenna to a desired frequency of operation. However, the capacitance value or range of the capacitance circuit is fixed once the IC is taped out and it might not be enough to achieve the required antenna tuning without using an external lumped matching component (i.e., discrete, lump capacitor or inductor).

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of design for conjugate matching the reactive impedance of an inductive loop antenna to the reactive impedance of an integrated circuit (IC) using distributed reactive loads are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments described herein include a technique for designing inductive loop antennas to conjugate match the reactive load of an integrated circuit (IC). The impedance $Z_{IC}$ looking into a connection terminal of an IC is defined by, $$Z_{IC} = R_{IC} + X_{IC}, \quad \text{(Eq. 1)}$$

where $R_{IC}$ is the real component (i.e., resistance) of the impedance and $X_{IC}$ is the imaginary component (i.e., reactance). Correspondingly, the impedance $Z_L$ of an inductive loop antenna is defined by, $$Z_L = R_L + X_L, \quad \text{(Eq. 1)}$$

where $R_L$ is the real component of the inductive loop antenna and $X_L$ is the imaginary component. Conjugate reactance matching is the equal (or substantially equal) but opposite matching of the $X_{IC}$ to $X_L$. In other words, $X_L$ substantially equals $-X_{IC}$. The conjugate reactance matching described herein serves to cancel out the reactance of the IC with selective design of the inductive loop antenna using distributed reactive loads. These distributed reactive loads facilitate frequency tuning of an inductive loop antenna to match the operational output frequency of a fixed design IC. Flexibility in the tuning of the inductive loop antenna facilitates recycling a previously designed IC without need of a new tape-out of the IC to alter its output impedance. In other words, embodiments of the present disclosure enable a simple, less expensive redesign to match a fixed design IC, as opposed a more complicated and expensive redesign of the IC to match a specific sized inductive loop antenna.

The distributed reactive loads described herein enable tuning of an inductive loop antenna without need of altering the overall size (e.g., diameter) of a corresponding simple inductive loop antenna. The described distributed reactive loads are implemented using signal trace sections that may form portions of the inductive loop antenna itself. As such, the distributed reactive loads need not include discrete, lump capacitors or inductors, such as discrete surface mount capacitors and inductors. The lack of discrete, lump components makes the described distributed reactive loads particularly well suited for use in size or form factor constrained applications. For example, embodiments described herein are well suited for use in miniaturized devices such as eye worn devices (e.g., contact lenses or intraocular lenses) or other body implantable devices (e.g., devices implanted in or under the skin) that employ wireless communication and/or wireless inductive charging. The use of discrete, lump components often cannot satisfy the size and comfort requirements of body mounted or body implanted devices, particularly eye worn devices.

The thin signal trace sections used to implement the distributed reactive loads have a lower profile and greater flexibility when compared to discrete, lump components. The flexibility of the signal traces lends itself well to body implantable devices that are rolled or folded during implantation. The flexibility is amendable to inductive loop antennas that are disposed on substrates that conform to a curvature, such as the spherical shape of a contact lens. There are sometimes requirements on how flexible/bendable a body mountable/implantable device should be. The use of a simple loop antenna or electrode can introduce waviness concerns into the device, which can be problematic for reliable manufacturing. In particular, contact lenses may include a loop or ring antenna that is manufactured in a flat process for cost savings, and then the loop antenna is transferred onto a curved surface to which the loop/ring antenna must conform. A continuous metal ring can make this reshaping problematic as the metal may bend differently to the underlying substrate. This can increase the thickness of the lens, lead to protrusions, and result in higher costs and lower manufacturing yields. In various embodiments, the distributed reactive loads described herein overcome this drawback of a simple, continuous inductive loop antenna by introducing breaks in the signal trace sections of the loop itself. These breaks provide natural flex zones to ameliorate tension or stress due to bending of the conductive signal traces of the antenna/electrode.

As mentioned, the techniques described herein are well suited to tune compact antennas. For example, these antennas may be inductive loop antennas that serve dual purposes of wireless inductive charging and backscatter wireless communications (e.g., near field communications). Such compact antennas are well suited for operation using wireless signals above 400 MHz (e.g., UHF or higher).

Figure 1:
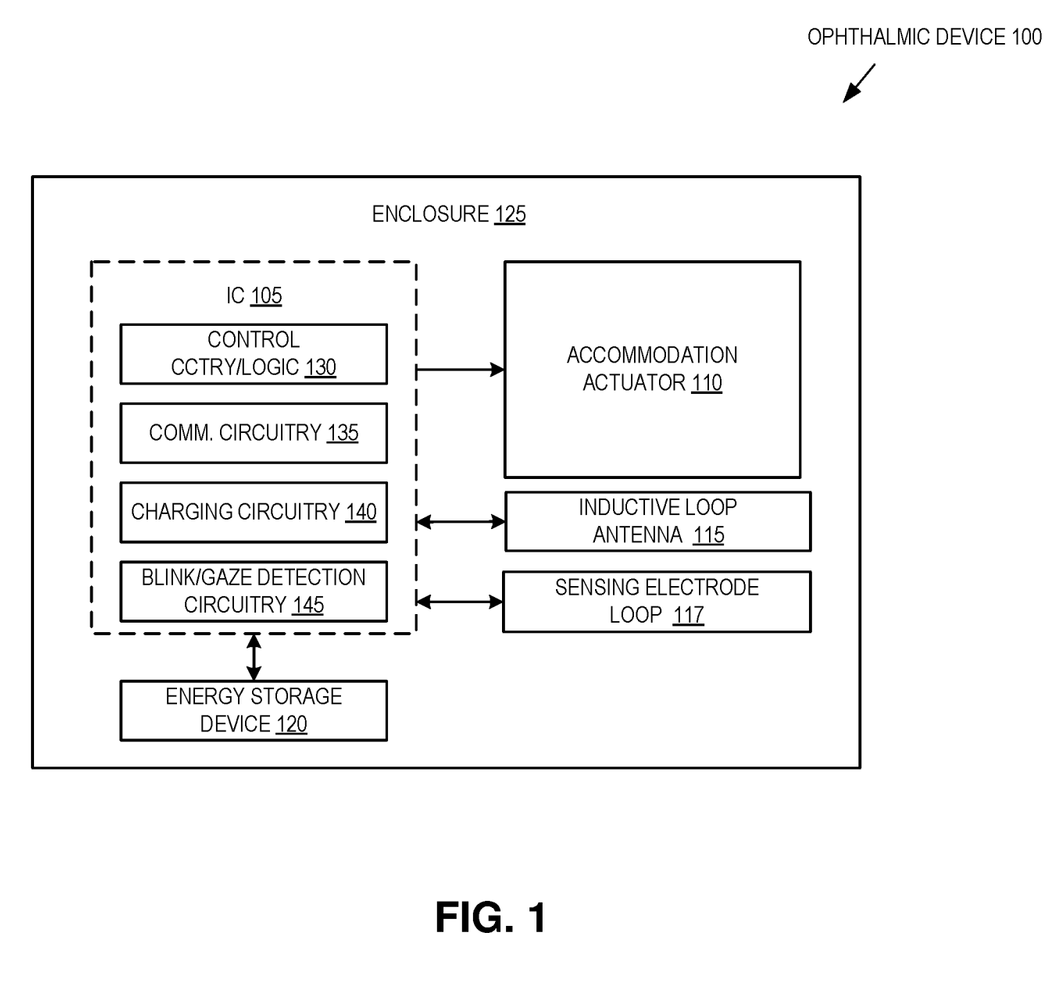
FIG. 1 is a functional block diagram of an ophthalmic device, in accordance with an embodiment of the disclosure

FIG. 1 is a functional block diagram of an ophthalmic device 100, in accordance with an embodiment of the disclosure. Ophthalmic device 100 represents just one example body mountable/implantable device and it should be appreciated that the techniques disclosed herein are not limited for use with just ophthalmic devices, such as a contact lens or intraocular lens. The illustrated embodiment of ophthalmic device 100 includes integrated circuit (IC) 105, an accommodation actuator 110, an inductive loop antenna 115, a sensing electrode loop 117, and an energy storage device 120 all sealed within an enclosure 125. The illustrated embodiment of IC 105 includes control circuitry/logic 130, communication circuitry 135, charging circuitry 140, and blink/gaze detection circuitry 145. It should be appreciated that FIG. 1 is a functional diagram and some of the illustrated components and circuitry may be implemented in hardware, software, or a combination of both. Furthermore, the physical components that implement the illustrated functions may be centralized, as illustrated, or distributed. In one embodiment, IC 105 is implemented within an application specific integrated circuit (ASIC) that is mounted on an annular substrate within enclosure 125.

The enclosure material, represented by enclosure 125, may function as a light transmissive lensing material and may form, at least in part, a sealed enclosure in which is disposed circuitry of ophthalmic device 100. The dielectric enclosure material may be fabricated of a variety of materials biocompatible for direct contact with a human eye, such as a polymeric material, a hydrogel, PMMA, silicone based polymers (e.g., fluoro-silicon acrylate), or otherwise. Enclosure material 125 may be in the form of a round lens with a concave curvature configured to mount to a corneal surface of an eye. The electronics may be disposed upon a substrate embedded within the one or more enclosure materials near a periphery of ophthalmic device 100 to avoid interference with incident light received closer to the central region of the cornea.

Control circuitry/logic 130 represents miscellaneous components for orchestrating the operation of ophthalmic device 100. For example, control circuitry/logic 130 may be implemented with a microcontroller, on-board memory storing various software instructions, and may also include hardware logic configured to perform specific functions. Communication circuitry 135 may include RF electronics to receive, and in some embodiments also transmit, wireless data over inductive loop antenna 115. In one embodiment, communication circuitry 135 is a RF identification tag and inductive loop antenna 115 is a backscatter loop antenna. Charging circuitry 140 may include RF power rectification circuitry to harvest power from an RF carrier wave incident upon inductive loop antenna 115 and charge energy storage device 120 (e.g., on-board battery, storage capacitor, etc.). In the illustrated embodiment, blink/gaze detection circuitry 145 is coupled to sensing electrode loop 117 to detect changes in an impedance of sensing electrode loop 117, which are dependent upon changes in an amount an eyelid overlaps sensing electrode loop 117. The eyelid overlap detection may be used to generate a blink detect signal or even a signal correlated to gaze detection. These signals may then be used by control logic 130 to provide feedback control over the optical power of accommodation actuator 110. Accommodation actuator 110 is a dynamic lens, such as a liquid crystal (LC) cell, a multi-layer LC diffractive lensing structure, an electrowetting lens, or otherwise.

Figure 2A:
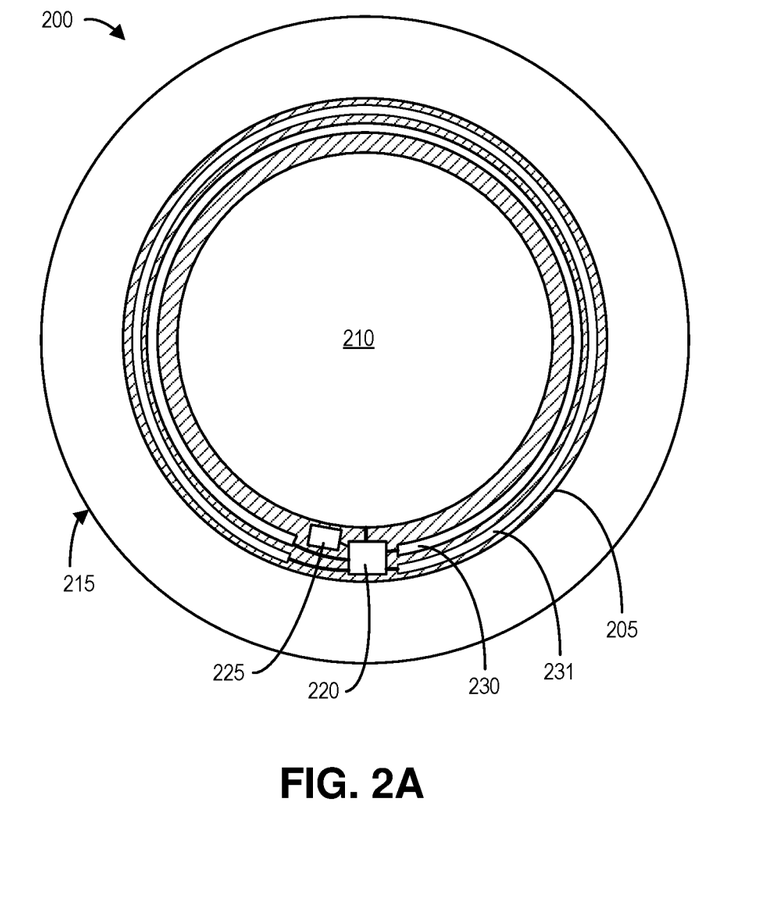
FIGS. 2A & 2B are plan and perspective view illustrations of a contact lens, in accordance with an embodiment of the disclosure.
Figure 2B:
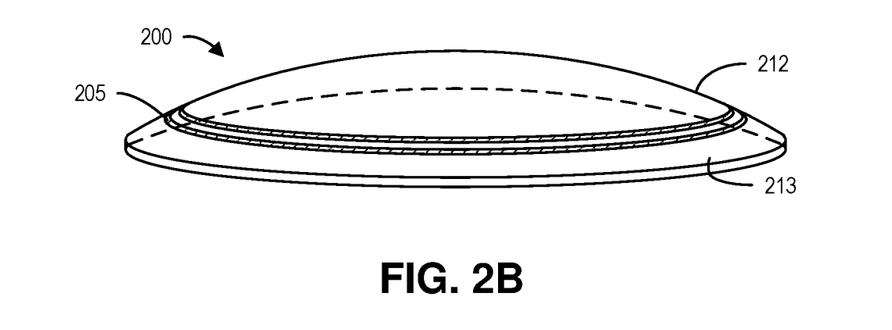

FIGS. 2A and 2B are illustrations of a contact lens system 200 including a dynamic diffractive liquid crystal lens, in addition to an inductive loop antenna. System 200 is one possible implementation of ophthalmic device 100 illustrated in FIG. 1. The illustrated embodiment of contact lens system 200 includes an annular substrate 205 (or other surface), a dynamic lens 210, an enclosure 215, an IC 220, an energy storage device 225, a sensing electrode loop 230, and an inductive loop antenna 231. Enclosure 215 has a size and shape that mounts over the cornea of an eye. In the illustrated embodiment, enclosure 215 includes an anterior side 212 having a convex shape and a posterior side 213 having a concave shape. Of course, contact lens system 200 may assume other shapes and geometries including a piggyback configuration that attaches to a surface of an eye-mountable carrier substrate having an overall shape that resembles a conventional contact lens.

In the illustrated embodiment, inductive loop antenna 231 is a backscatter loop antenna that encircles sensor electrode loop 230, which is also an inductive loop. Sensing electrode loop 230 is one possible implementation of sensing electrode loop 117 while inductive loop antenna 231 is one possible implementation of inductive loop antenna 115. As illustrated, both loops 230 and 231 encircle dynamic lens 210 and couple to IC 220. In one embodiment, sensor electrode loop 230 is a differential electrode with its opposite ends coupled to differential inputs of an impedance sensor implemented with an oscillation circuit disposed within controller 220. As illustrated, inductive loop antenna 231 and sensing electrode loop 117 are both disposed on the annular shaped substrate 205 (or other surface), which may conform to the curvature (e.g., spherical contour) of the contact lens.

Figure 5A:
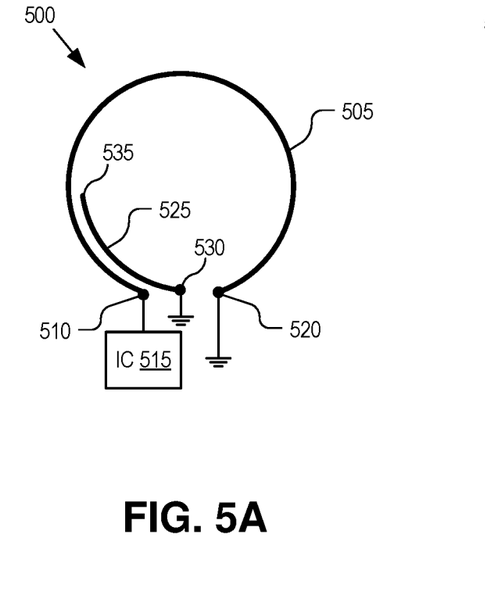
FIGS. 5A & 5B illustrate techniques of introducing a distributed shunt capacitance to an inductive loop antenna, in accordance with embodiments of the disclosure.
Figure 5B:
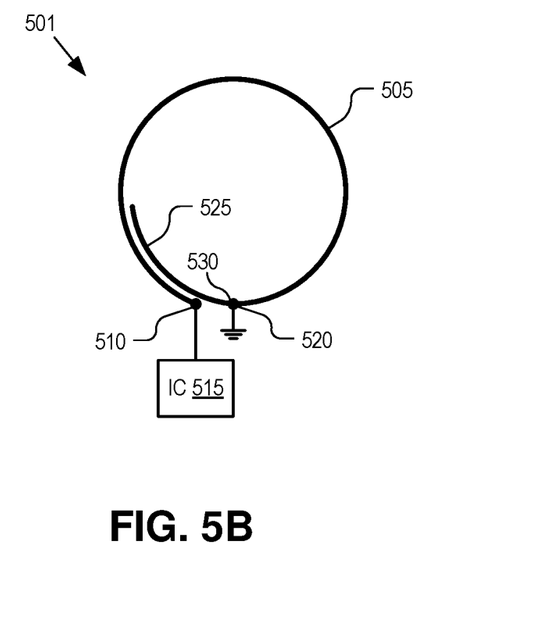
Figure 6A:
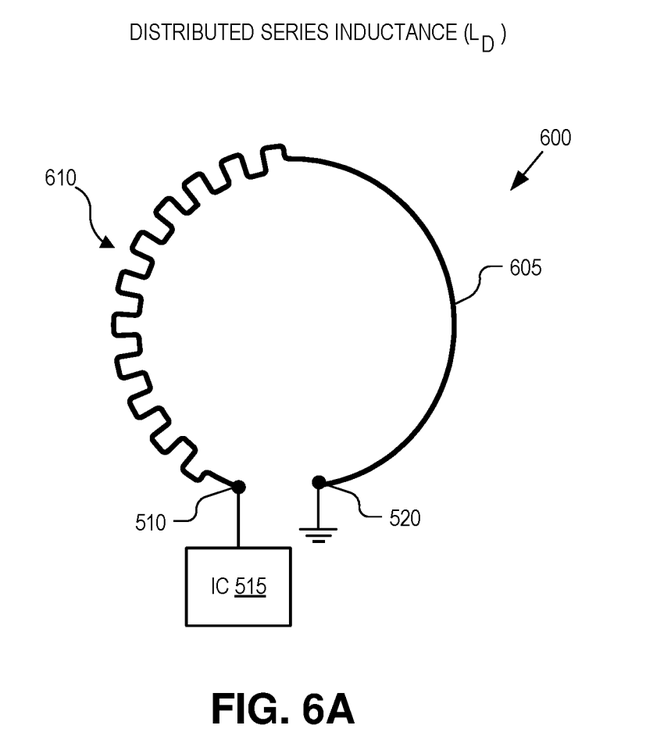
FIG. 6A illustrates a technique of introducing a distributed series inductance to an inductive loop antenna, in accordance with an embodiment of the disclosure.
Figure 7A:
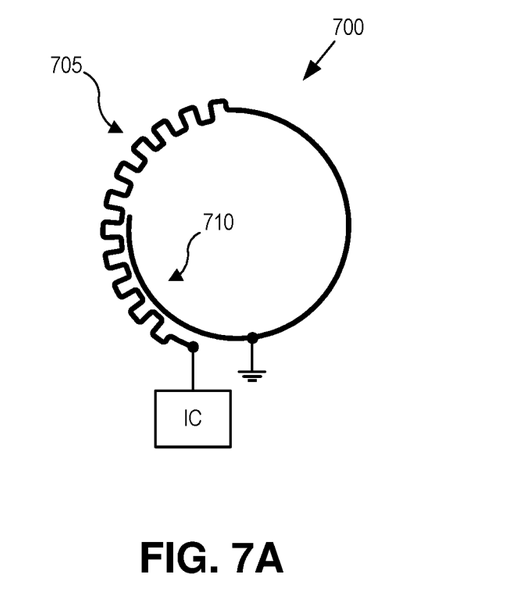
FIG. 7A illustrates how to integrate both a distributed inductive load and a distributed shunt capacitance into a single inductive loop antenna, in accordance with an embodiment of the disclosure.
Figure 7B:
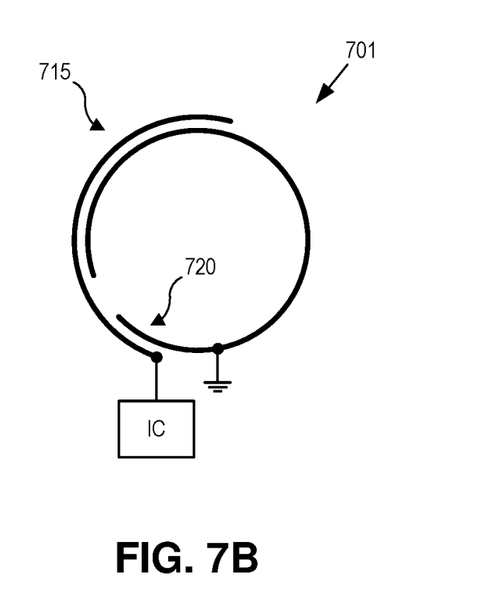
FIG. 7B illustrates how to integrate both a distributed series capacitance and a distributed shunt capacitance into a single inductive loop antenna, in accordance with an embodiment of the disclosure.

IC 220 may be an electronic component that is used across a variety of different body mountable/implantable devices, such as contact lens system 200, or may be used with a variety of different types or sizes of contact lenses. As such, conjugate reactance matching IC 220 to inductive loop antenna 231 may be a challenge with a fixed IC design. This is particularly so since the compact, curved, and slim form factor of a contact lens is not amenable to tuning these loops with discrete, lump capacitors/inductors (e.g., discrete surface mount capacitors/inductors) directly coupled to the loops. Accordingly, embodiments described herein use distributed reactive loads formed from the signal traces that make up inductive loop antenna 231 itself to tune inductive loop antenna 231 to IC 220. FIGS. 4A, 5A, 5B, and 6A illustrate different techniques for forming distributed reactive loads on inductive loop antenna 231. FIGS. 7A and 7B illustrate how the different distributed reactive loads can be combined and used together in various combinations. Although this disclosure discusses conjugate reactance matching of inductive loop antenna 231 to IC 220, it should be appreciated that these principles are equally applicable to conjugate reactance matching of sensing electrode loop 117 to IC 220 as well. In particular, the two inductive loops can form a highly coupled transformer circuit and thus their respective impedances (e.g., reactances) may be transferred into each other. Accordingly, in various embodiments, distributed reactive loads may be used in both inductive loops 230 and/or 231 to change their respective reactances, which are transferred to each other via a coupling factor. These transferred reactances can be used to further tune the resonant frequencies of each inductive loop in a desired manner.

Figure 3:
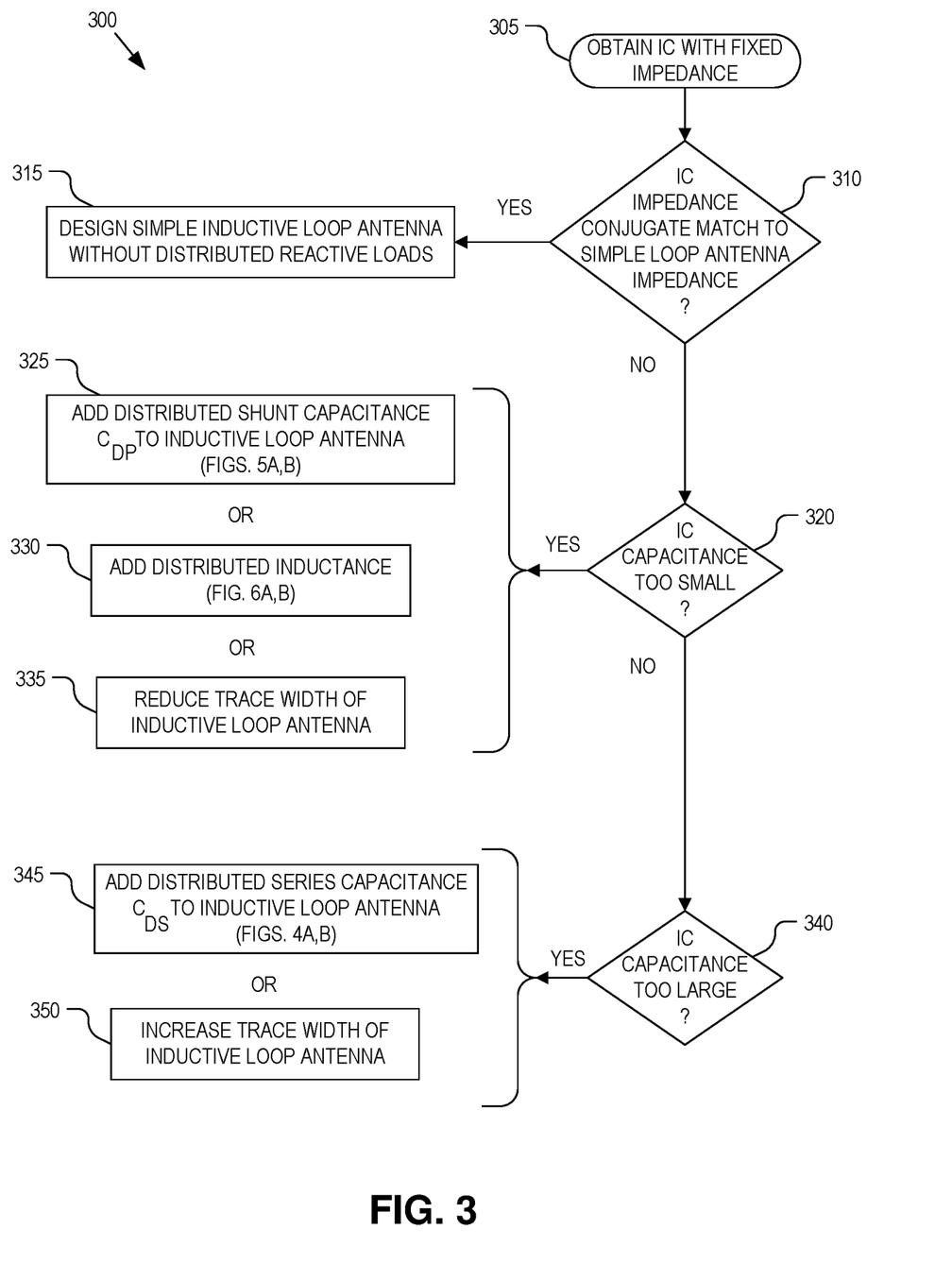
FIG. 3 is a flow chart illustrating a design technique for conjugate matching the reactive impedance of an inductive loop antenna to the reactive impedance of an integrated circuit (IC) using distributed reactive loads, in accordance with an embodiment of the disclosure.

FIG. 3 is a flow chart illustrating a design technique for conjugate matching the reactive impedance of inductive loop antenna 231 to the reactive impedance of IC 220 using distributed reactive loads, in accordance with an embodiment of the disclosure. The order in which some or all of the process blocks appear in process 300 should not be deemed limiting. Rather, one of ordinary skill in the art having the benefit of the present disclosure will understand that some of the process blocks may be executed in a variety of orders not illustrated, or even in parallel.

In a process block 305, a design for an IC (such as IC 105 or 220) having a fixed impedance is received. The design may already be taped-out, or even represent a prefabricated chip and thus altering the impedance at its input/output terminals may not be possible or practical. In a decision block 310, if the IC impedance is a conjugate reactance match with a simple loop antenna of appropriate size for the system design constraints, then process 300 proceeds to process block 315 where a simple inductive loop antenna (i.e., inductive loop antenna without distributed reactive loads) is designed, and then ultimately fabricated. Alternatively, if the reactance of a simple inductive loop antenna does not sufficiently conjugate match (e.g., within application tolerances) the reactance of the IC, then process 300 continues to decision blocks 320 and/or 340 to select and integrate appropriate distributed reactive loads into the inductive loop antenna.

Figure 5C:
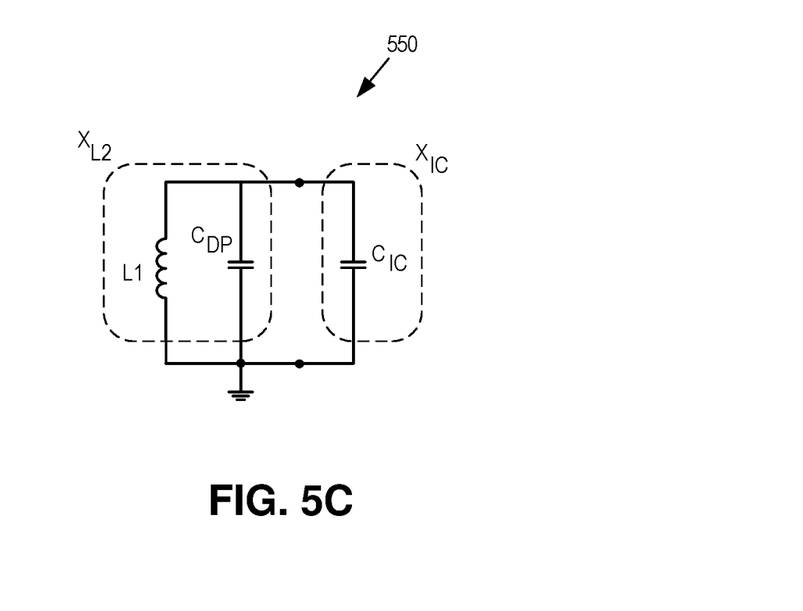
FIG. 5C is a circuit diagram illustrating the introduction of a distributed shunt capacitance to an inductive loop antenna, in accordance with an embodiment of the disclosure.

In decision block 320, if the capacitance of the IC is too small to be substantially conjugate matched by the reactance of a simple inductive loop antenna, then process 300 continues to one or more of process block 325-335. One, some, or all of the design adjustments described in each of process blocks 325-335 may be implemented to adjust the reactance of an inductive loop antenna to provide adequate conjugate reactance matching. In process block 325, a distributed shunt capacitance $C_{DP}$ may be added to an inductive loop antenna (such as inductive loop antenna 231). FIGS. 5A and 5B illustrates two techniques for adding distributed shunt capacitance $C_{DP}$ to an inductive loop antenna having an inductance L1. As illustrated in FIG. 5C, distributed shunt capacitance $C_{DP}$ is introduced as a parallel capacitance to inductance L1 to collectively form the total reactance $X_{L2}$, which is then selected to conjugate match the IC reactance $X_{IC}$. Accordingly, the distributed shunt capacitance $C_{DP}$ may be added to adjust the total reactance $X_{L2}$ of an inductive loop antenna to thereby improve conjugate reactance matching.

In the embodiment of FIG. 5A, inductive loop antenna 500 includes a first signal trace section 505 coupled at a first end 510 to an IC 515 (e.g., IC 105 or 220) and at a second end 520, opposite first end 510, to a fixed potential such as ground. A second signal trace section 525 is disposed on a common substrate (e.g., substrate 205) with, and adjacent to, first signal trace section 505. Accordingly, signal trace sections 505 and 525 are adjacent-lapping sections. A first end 530 of second signal trace section 525 is also coupled to a fixed potential, such as ground, while its opposite end 535 floats.

Signal trace sections 505 and 525 are physically distinct and separate signal traces; however, the presence of second signal trace section 525 routed along side of signal trace section 505 introduces the distributed shunt (parallel) capacitance $C_{DP}$. In the illustrated embodiment, second signal trace section 525 is routed parallel to first signal trace section 505; however, in other embodiments, the separation gap may vary. The length of the adjacent-lapping section varies the magnitude of $C_{DP}$.

FIG. 5B illustrates another physical implementation of an inductive loop antenna 501 for introducing distributed shunt capacitance $C_{DP}$. Inductive loop antenna 501 is similar to inductive loop antenna 500 except that signal trace sections 505 and 525 form a single continuous signal trace (e.g., physically monolithic conductive member). In other words, first end 530 of second signal trace section 525 couples to second end 520 of first signal trace section 505 at a connection point to ground. Both inductive loop antennas 500 and 501 introduce a distributed shunt capacitance $C_{DP}$ in parallel to an inductance L1, as represented in the circuit diagram 550 of FIG. 5C.

Figure 6B:
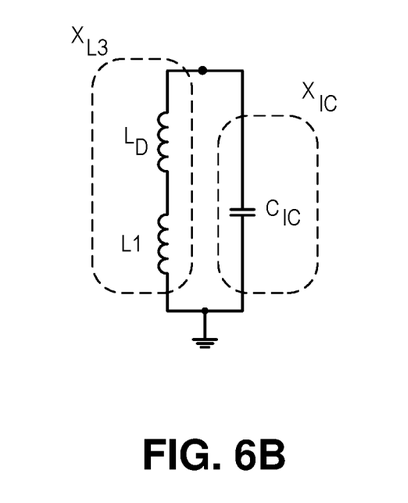
FIG. 6B is a circuit diagram illustrating the introduction of a distributed series inductance to an inductive loop antenna, in accordance with an embodiment of the disclosure.

Returning to FIG. 3, as an addition or alternative to adding a distributed shunt capacitance, a distributed inductance may be added in a process block 330 to further conjugate match the reactance of an IC with an otherwise too small capacitance. FIG. 6A illustrates a technique for adding distributed inductance $L_D$ to the inductance L1 of an inductive loop antenna. As illustrated in FIG. 6B, distributed inductance $L_D$ is introduced in series with the inductance L1 to collectively present a total reactance $X_{L3}$ to the connection terminals of IC 515, which total reactance $X_{L3}$ is selected to substantially conjugate match the IC reactance $X_{IC}$. Accordingly, the distributed inductance $L_D$ may be added to adjust the total reactance $X_{L3}$ of inductive loop antenna 600 to thereby improve conjugate reactance matching.

Inductive loop antenna 600 includes a continuous signal trace 605 that is routed generally along a loop path between first end 510 coupled to IC 515 and second end 520 coupled to a fixed potential such as ground. Continuous signal trace 605 includes a meandering section 610 that deviates or dithers about the general loop path for a portion of continuous signal trace 605. This meandering introduces the additional series distributed inductance $L_D$. The length of meandering section 610 varies the magnitude of $L_D$.

Again returning to FIG. 3, as an addition or alternative to adding a distributed shunt capacitance or distributed series inductance, the width of signal trace sections of the inductive loop antenna may also be reduced to improve conjugate reactive matching to an IC having a capacitance that is too small (process block 335).

Figure 4A:
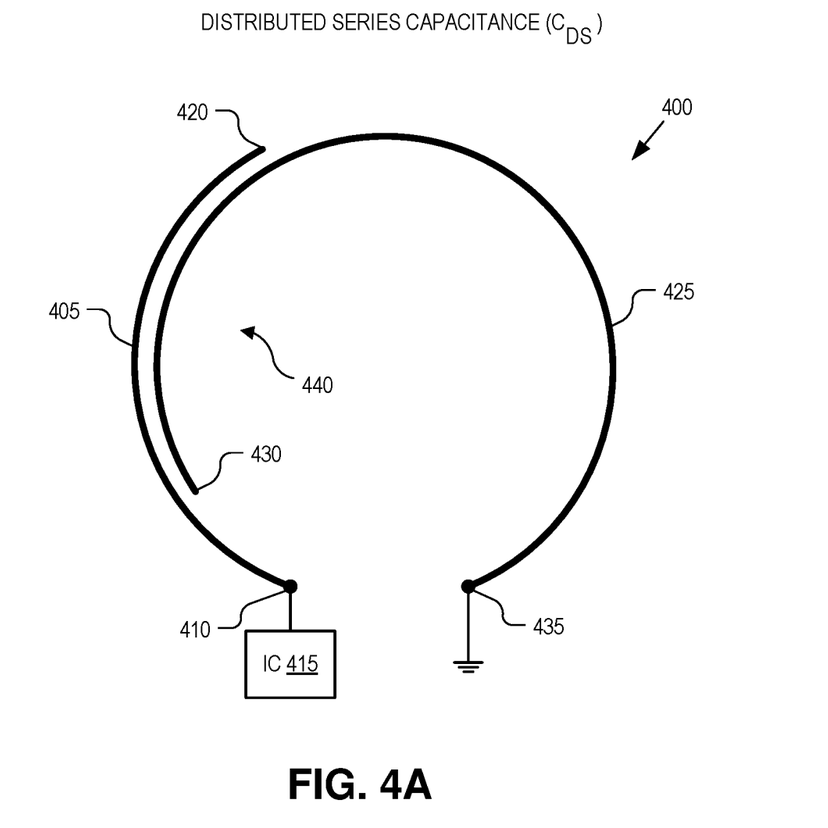
FIG. 4A illustrates a technique of introducing a distributed series capacitance to an inductive loop antenna, in accordance with an embodiment of the disclosure.
Figure 4B:
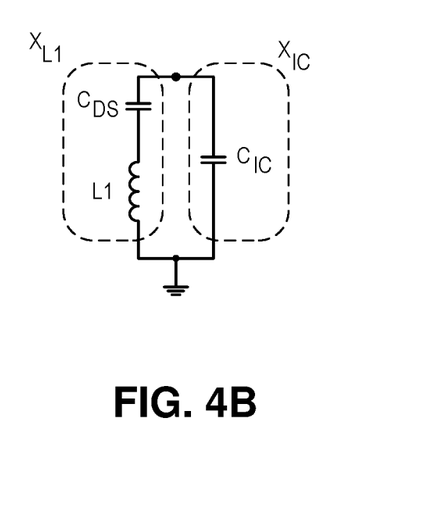
FIG. 4B is a circuit diagram illustrating the introduction of a distributed series capacitance to an inductive loop antenna, in accordance with an embodiment of the disclosure.

On the other hand, if the capacitance of the IC is too large for conjugate reactance matching to a simple inductive loop antenna (decision block 340), then process 300 continues to process blocks 345-350. One or both of the design adjustments described in each of process blocks 345 and 350 may be implemented to adjust the reactance of an inductive loop antenna to provide adequate conjugate reactance matching. In process block 345, a distributed series capacitance $C_{DS}$ may be added to an inductive loop antenna (such as inductive loop antenna 231). FIGS. 4A illustrate a technique for adding a distributed series capacitance $C_{DS}$ to an inductive loop antenna having an inductance L1. As illustrated in FIG. 4B, distributed series capacitance $C_{DS}$ is introduced as a series capacitance to inductance L1 to collectively form the total reactance $X_{L1}$, which is then selected to conjugate match the IC reactance $X_{IC}$. Accordingly, the distributed shunt capacitance $C_{DS}$ may be added to adjust the total reactance $X_{L1}$ of an inductive loop antenna to thereby improve conjugate reactance matching.

In the embodiment of FIG. 4A, inductive loop antenna 400 includes a first signal trace section 405 coupled at a first end 410 to an IC 415 (e.g., IC 105 or 220) and otherwise floating at a second end 420, opposite first end 410. A second signal trace section 425 is disposed on a common substrate or surface (e.g., substrate 205) and completes the general loop path started by the first signal trace section 405. A first end 430 of second signal trace section 425 floats while a second end 435, opposite the first end, is coupled to a fixed potential, such as ground. The two signal trace section 405 and 425 have an adjacent-lapping section 440 where the two traces run sufficiently close to each other to form a capacitive coupling therebetween. In the illustrated embodiment, the signal trace sections 405 and 425 run offset, but parallel to each other along adjacent-lapping section 440. Signal trace sections 405 and 425 are physically distinct and separate signal traces; however, the presence of second signal trace section 425 routed along side of signal trace section 405 introduces the distributed series capacitance $C_{DS}$. In the illustrated embodiment, second signal trace section 425 is routed parallel to first signal trace section 405 in the adjacent-lapping section 440; however, in other embodiments, the separation gap may vary. The length of adjacent-lapping section 440 varies the magnitude of $C_{DS}$. In some embodiments, adjacent-lapping section 440 may also be interdigitated (e.g., both signal traces meandered next to each other) to increase capacitance.

Although FIG. 4A illustrates adjacent-lapping section 440 as occurring on the same plane with the respective signal traces running lateral to each other, adjacent-lapping section 440 may also be implemented by running the respective signal traces on different planes (e.g., underneath or above each other). Accordingly, the term "adjacent" is not limited to signal traces that are adjacent on a common plane, but also includes signal traces that are adjacent but on different planes. Different planes may be achieved using a multiple layer fabrication process using signal vias.

Returning to FIG. 3, as an addition or alternative to adding a distributed series capacitance, the width of signal trace sections of the inductive loop antenna may also be increased to improve conjugate reactive matching to an IC having a capacitance that is too large (process block 350).

As mentioned above, the various techniques for introducing distributed reactive loads may be combined to achieve a desired total reactance $X_L$ for improve conjugate matching. For example, FIG. 7A illustrates how to integrate both a distributed inductive load (meandering 705) with and a distributed shunt capacitance (adjacent-lapping section 710) into a single inductive loop antenna 700. Similarly, FIG. 7B illustrates how to integrate both a distributed series capacitance (adjacent-lapping section 715) with a distributed shunt capacitance (adjacent-lapping section 720) into a single inductive loop antenna 701. Other combinations may be implemented.

Figure 8:
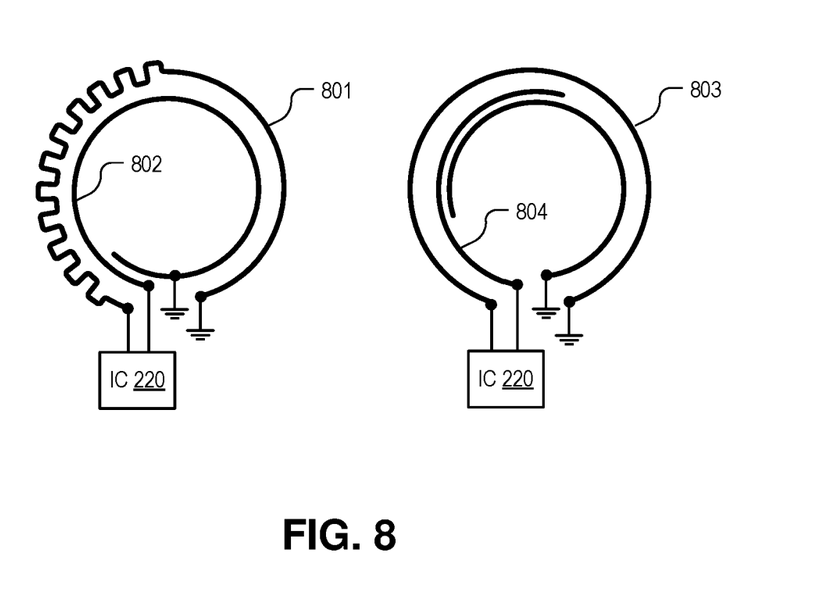
FIG. 8 illustrates how to use distributed reactive loads on an inductive loop antenna and/or an interiorly/exteriorly positioned sensing electrode loop to offset their respectively resonant frequencies, in accordance with an embodiment of the disclosure.

FIG. 8 illustrates how to use distributed reactive loads on an inductive loop antenna and/or an interiorly positioned sensing electrode loop to offset their respectively resonant frequencies, in accordance with an embodiment of the disclosure. For example, outer inductive loop antenna 801 (corresponding to inductive loop antenna 231) may be meandered to introduce a series inductance while inner inductive loop electrode 802 (corresponding to inductive loop electrode 230) may include a distributed shunt capacitance. These distributed reactive loads (or other combinations thereof) may be introduced to one or both of the inductive loop antennas/electrodes to skew/shift their respective resonant frequencies away from each other providing greater isolation. In this manner, inductive loop electrode 230 may be designed to have reduced coupling with inductive loop antenna 231 and thus present a reduced parasitic load on inductive loop antenna 231 at the communication frequency band of inductive loop antenna 231. Correspondingly, inductive loop antenna 231 may be designed to present a reduced parasitic load on inductive loop electrode 230 at the sensing frequency of inductive loop electrode 230. FIG. 8 also illustrates an example wherein inner inductive loop electrode 804 includes a distributed series capacitance while outer inductive loop antenna 803 is a simple loop antenna. Of course, other combinations may be implemented to achieve the desired resonant frequencies for each loop after accounting for the coupling factor between the loops. While FIGS. 2A and 8 illustrate an inductive loop electrode for sensing positioned within an inductive loop antenna for communications, the techniques disclosed herein are equally applicable to positioning the inductive loop antenna interiorly to the inductive loop electrode.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A device for implanting into or mounting onto a body, the device comprising:
   an enclosure;
   an inductive loop antenna disposed on a surface within the enclosure, the inductive loop antenna including one or more distributed reactive loads disposed along the inductive loop antenna that adjust a reactance of the inductive loop antenna, wherein the one or more distributed reactive loads include signal trace sections that run along, or adjacent to, the surface upon which the inductive loop antenna is disposed; and
   an integrated circuit (IC) disposed within the enclosure and coupled to the inductive loop antenna, the IC including communication circuitry coupled to the inductive loop antenna to wirelessly communicate over the inductive loop antenna,
   wherein the one or more distributed reactive loads adjust the reactance of the inductive loop antenna to improve conjugate reactance matching of the inductive loop antenna to the IC,
   wherein the signal trace sections of the one or more distributed reactive loads include a first signal trace section and a second signal trace section having at least a portion of the second signal trace section routed adjacent to the first signal trace section to form an adjacent-lapping section,
   wherein the one or more distributed reactive loads comprises a distributed series capacitive load that couples in series with an inductance of the inductive loop antenna, wherein the first signal trace section is coupled to the IC and the second signal trace section is coupled to a ground, and wherein the first and second signal trace sections collectively form the inductive loop antenna.

2. The device of claim 1, wherein the one or more distributed reactive loads do not include a discrete surface mount capacitor or a discrete surface mount inductor.

3. The device of claim 1, wherein the first and second signal trace sections are disposed on and routed along the surface.

4. The device of claim 3, wherein the portion of the second signal trace section is routed adjacent and parallel to, but offset from, the first signal trace section.

5. The device of claim 3, wherein the one or more distributed reactive loads also includes a distributed shunt capacitive load that couples in parallel with an inductance of the inductive loop antenna, wherein a third signal trace section is coupled to the IC at a first end and coupled to a ground at a second end opposite the first end, and wherein a fourth signal trace section is coupled to the ground at a first end of the fourth signal trace section and floats at a second end of the fourth signal trace section.

6. The device of claim 5, wherein the fourth signal trace section is physically distinct and separate from the third signal trace section.

7. The device of claim 5, wherein the third and fourth signal trace sections comprise a single continuous signal trace such that the second end of the third signal trace section is coupled to the first end of the fourth signal trace section at a connection point to the ground.

8. The device of claim 1, wherein the one or more distributed reactive loads also includes a distributed inductive load that couples in series with an inductance of the inductive loop antenna, and wherein the distributed inductive load comprises a meandering section of a continuous signal trace that is routed generally along a loop path coupled at a first end to the IC and coupled at a second end, opposite the first end, to a ground.

9. The device of claim 1, further comprising:
   an energy storage device disposed within the enclosure, wherein the IC further includes charging circuitry coupled to the inductive loop antenna and to the energy storage device to harvest wireless power incident on the inductive loop antenna for charging the energy storage device.

10. The device of claim 9, wherein the device comprises a contact lens, the surface comprises a substrate having an annular shape, and wherein the inductive loop antenna and the substrate conform to a curvature of the contact lens.

11. The device of claim 10, further comprising:
    a sensing electrode loop disposed within the inductive loop antenna and coupled to an oscillator circuit within the IC for monitoring eyelid overlap; and
    one or more additional distributed reactive loads disposed along the sensing electrode loop and configured to adjust a reactance of the sensing electrode loop to shift a first resonant frequency of the sensing electrode loop away from a second resonant frequency of the inductive loop antenna.

12. An ophthalmic device, comprising:
    an enclosure sized and shaped for implantation into or surface mounting onto an eye;
    an energy storage device disposed within the enclosure;
    a substrate disposed within the enclosure;
    an inductive loop antenna disposed on the substrate within the enclosure, the inductive loop antenna including one or more distributed reactive loads disposed along the inductive loop antenna that adjust a reactance of the inductive loop antenna, wherein the one or more distributed reactive loads include:
      a first signal trace section routed on and along the substrate; and
      a second signal trace section disposed on and routed along the substrate with at least a portion of the second signal trace section routed adjacent to the first signal trace section to form an adjacent lapping-section; and
    an integrated circuit (IC) disposed within the enclosure and coupled to the inductive loop antenna and the energy storage device, the IC including:

charging circuitry coupled to the inductive loop antenna to harvest wireless power incident on the inductive loop antenna for charging the energy storage device; and communication circuitry coupled to the inductive loop antenna to wirelessly communicate over the inductive loop antenna, wherein the one or more distributed reactive loads adjust the reactance of the inductive loop antenna to improve conjugate reactance matching of the inductive loop antenna to the IC, wherein the one or more distributed reactive loads comprises a distributed shunt capacitive load that couples in parallel with an inductance of the inductive loop antenna, wherein the first signal trace section is coupled to the IC at a first end and coupled to a ground at a second end opposite the first end, and wherein the second signal trace section is coupled to the ground at a first end and floats at a second end.

13. The ophthalmic device of claim 12, wherein the portion of the second signal trace section is routed adjacent and parallel to, but offset from, the first signal trace section.

14. The ophthalmic device of claim 12, wherein the one or more distributed reactive loads also includes a distributed series capacitive load that couples in series with an inductance of the inductive loop antenna, wherein a third signal trace section is coupled to the IC and a fourth signal trace section is coupled to a ground.

15. The ophthalmic device of claim 12, wherein the second signal trace section is physically distinct and separate from the first signal trace section.

16. The ophthalmic device of claim 15, wherein the first and second signal trace sections comprise a single continuous signal trace such that the second end of the first signal trace section is coupled to the first end of the second signal trace section at a connection point to the ground.

17. The ophthalmic device of claim 12, wherein the one or more distributed reactive loads comprises a distributed inductive load that couples in series with an inductance of the inductive loop antenna, and wherein the distributed inductive load comprises a meandering section of a continuous signal trace that is routed generally along a loop path coupled at a first end to the IC.

18. The ophthalmic device of claim 12, wherein the ophthalmic device comprises a contact lens, wherein the substrate has a general annular shape, and wherein the inductive loop antenna and the substrate conform to a curvature of the contact lens.

19. The ophthalmic device of claim 18, further comprising:

a sensing electrode loop disposed within the inductive loop antenna and coupled to an oscillator circuit within the IC for monitoring eyelid overlap;

one or more additional distributed reactive loads disposed along the sensing electrode loop and configured to adjust a reactance of the sensing electrode loop that is transferred to the inductive loop antenna via a coupling factor to thereby adjust a resonant frequency of the inductive loop antenna.

20. A device for implanting into or mounting onto a body, the device comprising:

an enclosure;

an inductive loop antenna disposed on a surface within the enclosure, the inductive loop antenna including one or more distributed reactive loads disposed along the inductive loop antenna that adjust a reactance of the inductive loop antenna, wherein the one or more distributed reactive loads include signal trace sections that run along, or adjacent to, the surface upon which the inductive loop antenna is disposed; and an integrated circuit (IC) disposed within the enclosure and coupled to the inductive loop antenna, the IC including communication circuitry coupled to the inductive loop antenna to wirelessly communicate over the inductive loop antenna, wherein the one or more distributed reactive loads adjust the reactance of the inductive loop antenna to improve conjugate reactance matching of the inductive loop antenna to the IC, wherein the signal trace sections of the one or more distributed reactive loads include a first signal trace section and a second signal trace section having at least a portion of the second signal trace section routed adjacent to the first signal trace section to form an adjacent-lapping section, wherein the one or more distributed reactive loads comprises a distributed shunt capacitive load that couples in parallel with an inductance of the inductive loop antenna, wherein the first signal trace section is coupled to the IC at a first end and coupled to a ground at a second end opposite the first end, and wherein the second signal trace section is coupled to the ground at a first end of the second signal trace section and floats at a second end of the second signal trace section.

21. A device for implanting into or mounting onto a body, the device comprising:

an enclosure;

an inductive loop antenna disposed on a surface within the enclosure, the inductive loop antenna including one or more distributed reactive loads disposed along the inductive loop antenna that adjust a reactance of the inductive loop antenna, wherein the one or more distributed reactive loads include signal trace sections that run along, or adjacent to, the surface upon which the inductive loop antenna is disposed; and an integrated circuit (IC) disposed within the enclosure and coupled to the inductive loop antenna, the IC including communication circuitry coupled to the inductive loop antenna to wirelessly communicate over the inductive loop antenna, wherein the one or more distributed reactive loads adjust the reactance of the inductive loop antenna to improve conjugate reactance matching of the inductive loop antenna to the IC, wherein the one or more distributed reactive loads comprises a distributed inductive load that couples in series with an inductance of the inductive loop antenna, and wherein the distributed inductive load comprises a meandering section of a continuous signal trace that is routed generally along a loop path coupled at a first end to the IC and coupled at a second end, opposite the first end, to a ground.

* * * * *